United States Patent
Deller et al.

(10) Patent No.: US 9,311,707 B2
(45) Date of Patent: Apr. 12, 2016

(54) SYSTEM AND METHOD FOR ATTENUATION CORRECTION OF PHANTOM IMAGES

(71) Applicant: GENERAL ELECTRIC COMPANY, Schenectady, NY (US)

(72) Inventors: Timothy Wayne Deller, Waukesha, WI (US); Michael Lee Spohn, Waukesha, WI (US); Sonal Ambwani, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 211 days.

(21) Appl. No.: 14/039,059

(22) Filed: Sep. 27, 2013

(65) Prior Publication Data

US 2015/0090890 A1 Apr. 2, 2015

(51) Int. Cl.

| | |
|---|---|
| G01T 1/164 | (2006.01) |
| G06T 7/00 | (2006.01) |
| G01T 1/169 | (2006.01) |
| A61B 6/03 | (2006.01) |
| A61B 5/055 | (2006.01) |
| A61B 5/00 | (2006.01) |
| A61B 6/00 | (2006.01) |

(52) U.S. Cl.
CPC ............. G06T 7/0024 (2013.01); A61B 5/0035 (2013.01); A61B 5/055 (2013.01); A61B 6/037 (2013.01); A61B 6/4417 (2013.01); A61B 6/5205 (2013.01); A61B 6/5247 (2013.01); A61B 6/5258 (2013.01); A61B 6/583 (2013.01); G01T 1/169 (2013.01); A61B 6/4275 (2013.01)

(58) Field of Classification Search
CPC .. G06T 7/0024; A61B 6/5258; A61B 6/5205; A61B 6/5247; A61B 6/583; A61B 6/4417; A61B 6/037; A61B 5/055; A61B 5/0035; A61B 6/4275; G01T 1/169
USPC ............................ 250/363.01–36.09, 363.13
See application file for complete search history.

(56) References Cited

U.S. PATENT DOCUMENTS

| | | | |
|---|---|---|---|
| 7,737,406 B2 * | 6/2010 | Vija et al. | 250/363.04 |
| 2006/0145082 A1 | 7/2006 | Stearns et al. | |
| 2011/0164801 A1 * | 7/2011 | Gagnon et al. | 382/131 |
| 2012/0263360 A1 * | 10/2012 | Zhu et al. | 382/131 |

OTHER PUBLICATIONS

Palmeri et al., A Finite-Element Method Model of Soft Tissue Response to Impulsive Acoustic Radiation Force, Oct. 2005, IEEE Trans Ultrason Ferroelectr Freq Control. 52(10): 1699.*

Ziegler, Susanne, et al., Systematic Evaluation of Phantom Fluids for Simultaneous PET/MR Hybrid Imaging, Proc. Intl. Soc, Mag, Reson. Med 20 (2012), p. 2722.

Delso, Gaspar et al., Performance Measurements of the Siemens mMR Integrated Whole-Body PET/MR Scanner, The Journal of Nuclear Medicine, vol. 52, No. 12, Dec. 2011, pp. 1914-1922.

* cited by examiner

*Primary Examiner* — David Porta
*Assistant Examiner* — Gisselle Gutierrez
(74) *Attorney, Agent, or Firm* — Grogan, Tuccillo & Vanderleeden, LLP

(57) ABSTRACT

A method for attenuation correction of a phantom image in a PET imaging system includes obtaining raw scan data of a scanned phantom, a non attenuation corrected template image of a stock phantom of like type to the scanned phantom, and an attenuation map of the stock phantom. The method further includes generating a non-attenuation corrected raw image of the scanned phantom based on the raw scan data, registering the template image and attenuation map to the raw image through a rigid image transform, and applying the registered attenuation map to the raw scan data to enable reconstruction of an attenuation corrected final image.

18 Claims, 3 Drawing Sheets

SYSTEM AND METHOD FOR ATTENUATION CORRECTION OF PHANTOM IMAGES

BACKGROUND

1. Technical Field

Embodiments of the invention relate generally to system and method for medical imaging. Particular embodiments relate to systems and methods for attenuation correction of combined positron emission tomography/magnetic resonance imaging ("PET-MR").

2. Discussion of Art

Positron emission tomography ("PET") machines use one or more rings of scintillators or other detectors to generate electrical signals from gamma rays (photon pairs) that produced from the recombination of electrons, within a target material, and positrons, emitted from decay of a radionuclide packaged in a tracer compound. Typically, recombination events occur within about 1 mm from the radionuclide decay event, and the recombination photons are emitted in generally opposite directions to arrive at different detectors. Paired photon arrivals that occur within a detection window (usually less than a few nanoseconds apart) are counted as indicating a recombination event, and, on this basis, computed tomography algorithms are applied to the scintillator position and detection data in order to locate the various recombination events, thereby producing three-dimensional images of the tracer disposition within the target material.

Typically, the target material is body tissue, the tracer compound is a liquid analogue to a biologic fluid, and the radionuclide is disposed primarily in body tissues that make use of the biologic fluid. For example, a common form of PET makes use of fludeoxyglucose ($^{18}$F), which is analogous to glucose with the $^{18}$F radionuclide substituted for one of the hydroxyl groups ordinarily composing glucose. Fludeoxyglucose is preferentially absorbed by brain matter, by the kidneys, and by growing cells, e.g., metastasizing cancer cells. As a result, PET is frequently used for oncologic studies, for localizing particular organs, and for studying metabolic processes.

One challenge in obtaining desired PET image quality is that gamma rays, in the energy spectrum produced by positron-electron interactions, are easily attenuated by typical body tissues and are differently attenuated by different body tissues. Varying attenuation can diminish statistical confidence in the locations of recombination events, thereby making the computed image "fuzzier" than is desirable. Accordingly, it is highly desirable to provide means for attenuation correction ("AC").

For example, "phantoms" (artificial targets of known shape and material properties) can be imaged for evaluating PET performance, calibrating PET imaging software, and developing product capability specifications. Often, PET is combined with computed tomography ("CT"), which uses a moving X-ray source and detectors to obtain images of internal structures. X-rays are photons and are attenuated much like the lower-energy photons produced from positron-electron recombination events. Thus, AC algorithms, using CT data, can be useful for improving PET image quality in real time. Phantom scans in a PET-CT machine can be done using the same parameters and protocol as for a patient scan. The machine does not need adjustment to account for the phantom not being a patient.

Magnetic resonance imaging ("MR") uses magnetic sensors to detect rotating magnetic fields that are produced by nuclei that have odd atomic numbers, i.e., total number of neutrons and protons is not divisible by two, in response to alternately imposing and removing a magnetic field. Typically, MR is accomplished by imposing on a target material a strong, e.g., 1.5-3 Tesla, magnetic field that pulses or fluctuates at radio frequencies, e.g., 900 MHz. Field strength is important for establishing a steep field gradient, which helps in determining the location of nuclei. Radio frequency is important for amplifying the rotating fields, which are produced each time the fluctuating field is imposed. MR can also be accomplished using low-frequency, low-strength fields such as the geomagnetic field.

MR is frequently used for differentiating tissue types within a patient, and is also used for identifying fine detail structures. Typically, different pulse sequences are used for tissue differentiation. For example, a T1 pulse sequence can be used to obtain images with water appearing darker and fat brighter. On the other hand, a T2 pulse sequence can be used to obtain an image with fat darker, and water lighter.

One advantage of MR is that magnetic fields do not attenuate in body tissues, so that nucleus location can be determined (using Fourier analysis) based solely on frequency shifting between the imposed magnetic field and the response field. Another advantage is that by careful selection of pulse sequence, distinct tissues or materials can be highlighted.

PET and MR can be combined in a single apparatus (a "PET-MR scanner"). Such an apparatus provides fine detail, tissue differentiation, and metabolic data. However, because MR signals do not attenuate in the same way as PET or CT signals attenuate, and because MR signal return is highly dependent on the type of pulse sequence used (with each pulse sequence emphasizing a different material, whereas the PET signal is attenuated by every material intervening between a recombination event and a pair of detectors), it becomes difficult to obtain reliable AC of the PET signals based on MR signals from a single scan. For example, an MR image that is obtained using pulse sequences chosen to highlight radionuclide inserts within a phantom fill fluid, typically will not return a signal for the solid material of a phantom casing, which attenuates the PET signal from the fill fluid. Essentially, the MR image data is not useful for correcting the attenuated PET image data. Moreover, a schedule of MR pulse sequences, optimized for clinical scans (patient body materials) may not reliably return a usable image from a standard PET phantom.

Some of the difficulties in AC of PET images, in a PET-MR machine, can be overcome in case exact position of a phantom is known. Then prior knowledge of the phantom materials and structure can provide an ideal image, an AC parameters can be tuned to approximate the ideal image from the actually-obtained phantom image. This approach is similar to a manual registration technique in which a calculated attenuation map is manually registered to acquired data and used for reconstruction. Manual positioning of phantoms, or registration of an attenuation map with acquired data, however, is extremely difficult to accomplish with the precision needed for accurate AC.

Additionally, and more significantly, PET signal attenuation is very specific to patient anatomy and material properties. As already discussed, an MR image that does display the positron-absorbing phantom fluid, often does not display the photon-absorbing phantom casing. This problem is generalizable to clinical practice: Standard phantoms do not have the identically non-uniform distribution of tissue as is found in a patient. As such, attenuation of a phantom scan is not expected to accurately map to a subsequent patient scan, and phantom-based AC is not implemented using the same protocol as would be used in clinical settings for a patient scan.

As a result, other techniques for attenuation correction have been proposed. Many of these techniques depend upon receiving a locationally accurate MR signal from the liquid filling a PET phantom. For example, one approach involves mixing PET tracer in a solvent optimized for MR. The fluid body within a PET phantom can, however, exhibit MR image distortion for various reasons. Additionally, some phantoms are filled with a semi-solid gel, which may not return a quality MR image. Other problems with implementing this approach relate to the material specificity of MR pulse sequences.

In view of the above, aspects and embodiments of the present invention provide attenuation correction of a PET phantom image, in a PET-MR machine, without relying on the MR data.

BRIEF DESCRIPTION

In an embodiment of the invention, a method for attenuation correction of a phantom image in a PET imaging system includes obtaining raw scan data of a scanned phantom, a non attenuation corrected template image of a stock phantom of like type to the scanned phantom, and an attenuation map of the stock phantom. The method further includes generating a non-attenuation corrected raw image of the scanned phantom based on the raw scan data, registering the template image and attenuation map to the raw image through a rigid image transform, and applying the registered attenuation map to the raw scan data to enable reconstruction of an attenuation corrected final image.

In another embodiment of the invention, a PET imaging system includes a detector ring configured to produce signals indicating the detection of photons produced by positron-electron recombination and a processor connected in communication with the detector ring. The processor is configured to obtain a non attenuation corrected template image and an attenuation map of a stock phantom; obtain raw scan data of a scanned phantom of like type to the stock phantom; generate a non-attenuation corrected raw image of the scanned phantom based on the raw scan data; register the template image and attenuation map to the raw image; and generate a attenuation corrected final image from the raw scan data, using the registered attenuation map.

In embodiments of the invention, a processor, for communication with a detector ring that produces signals indicating the detection of photons from positron-electron recombination, is configured to receive as raw scan data the signals produced by the detector ring; generate a non-attenuation corrected raw image of a scanned phantom inserted through the detector ring, based on the raw scan data; obtain a non attenuation corrected template image and a computer model of a stock phantom, which is of like type to the scanned phantom; register the template image of the stock phantom to the raw image of the scanned phantom using a rigid image transform; and generate an attenuation corrected final image from the raw image, using the computer model of the stock phantom.

DRAWINGS

The present invention will be better understood from reading the following description of non-limiting embodiments, with reference to the attached drawings, wherein below:

DETAILED DESCRIPTION

Figure 1:
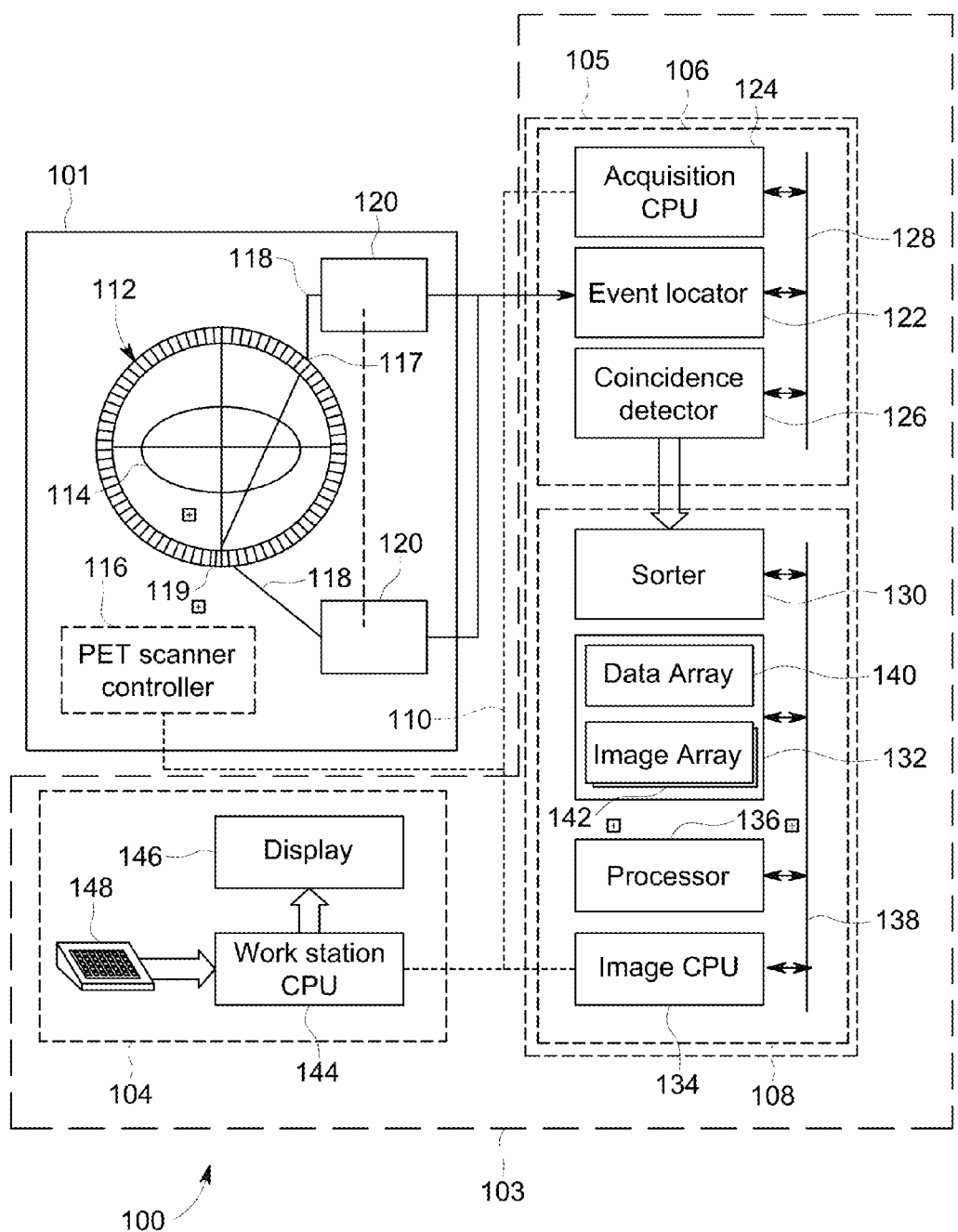
FIG. 1 shows in schematic view an exemplary embodiment of a PET imaging system, in which various aspects of the invention may be implemented.

Reference will be made below in detail to exemplary embodiments of the invention, examples of which are illustrated in the accompanying drawings. Wherever possible, the same reference characters used throughout the drawings refer to the same or like parts, without duplicative description. Exemplary embodiments of the present invention are described with respect to imaging a commercially-available phantom (i.e. a body of known shape and composition, usable for scan calibration, or the like), however, embodiments of the invention also are applicable for imaging any target for which a template image and attenuation map can be obtained. Embodiments of the invention relate to improving attenuation correction of PET phantom images.

FIG. 1 shows in schematic view an exemplary embodiment of a PET imaging system 100 in which various embodiments of the invention may be implemented. Many other types of PET imaging system are known, and the exemplary PET system 100 is merely one type of system in which the invention could be implemented. The exemplary PET system 100 includes a PET scanner 101 and an image processing system 103 to control normalization and image reconstruction processes. The image processing system 103 is also configured to correct losses in the normalization process due to dead time in detector blocks of PET scanner 101. The image processing system 103 includes an operator workstation 104, and a processor 105. The processor 105 includes a data acquisition processor 106 and an image reconstruction processor 108. The PET scanner 101, the operator workstation 104, the data acquisition processor 106, and the image reconstruction processor 108 are interconnected via a communication link 110 (e.g., a serial communication or wireless link).

The operation of the PET scanner 101 is controlled from the operator workstation 104. When the operator workstation 104 instructs the PET scanner 101 to perform a scan, the PET scanner 101 acquires scan data and transmits the scan data to the data acquisition processor 106. In response to commands from the operator workstation 104, the data acquired by the data acquisition processor 106 is reconstructed by the reconstruction processor 108.

The PET scanner 101 may operate using, for example, a plurality of detector rings 112. One such detector ring 112 is illustrated in FIG. 1. The exemplary detector ring 112 includes a central opening, in which a target 114 (e.g., a patient) may be positioned, using, for example, a motorized table, that is aligned with the central axis of detector ring 112. This motorized table moves the target 114 into the central opening of detector ring 112 in response to one or more commands received from operator workstation 104. A PET scanner controller 116, also referred to as a gantry controller, is provided (e.g., mounted) within the PET scanner 101. The PET scanner controller 116 responds to the commands received from the operator workstation 104 through the communication link 110. Therefore, operation of the PET scanner 101 is controlled from the operator workstation 104 through the PET scanner controller 116.

The detector ring 112 includes a plurality of detector elements 117 for performing a PET scan of target 114. Each detector element includes a set of scintillator crystals arranged in a matrix that is disposed in front of a plurality of photomultiplier tubes, e.g., four tubes. A photon colliding with a crystal on a detector is a "scintillation event." In response to each scintillation event, the photomultiplier tubes of the affected detector element 117 produce an analog signal on a communication line 118. Due to the paired nature of photons produced by positron-electron annihilations, scintillation events typically occur in pairs, within a brief time window determined by the photon speed and by the diameter of the detector ring, e.g., 50 to 70 cm. Therefore, for example, a particular detector element 117 might detect a first scintillation event at nearly the same time as another detector element 119 detected a second scintillation event; these two near-simultaneous events could form a "paired event" as further discussed below with reference to a coincidence detector 126.

The PET scanner 101 includes a set of acquisition circuits 120 to receive the analog signals produced by each scintillation event, and to produce digital signals indicating the affected detector element and total energy of each scintillation event, as well as a time when each scintillation event occurred. These digital signals are transmitted through a communication link, for example, a cable, to an event locator circuit 122 within the data acquisition processor 106.

The data acquisition processor 106 includes the event locator circuit 122, which may be integrated into an acquisition CPU 124, and which includes the coincidence detector 126. The event locator circuit 122 periodically samples the signals produced by the acquisition circuits 120, and passes the sampled signals into the coincidence detector 126, which receives the event data packets from event locator circuit 122 and determines if any two of the detected events are in coincidence or "paired."

Coincidence is determined by a number of factors. First, the time markers in each event data packet must be within a predetermined time period, for example, 12.5 nanoseconds, of each other. Events that cannot be paired are discarded. Events that can be paired are passed back to the event locator circuit 122, which identifies a straight line joining the two detectors that detected the paired events. This straight line localizes the event. In some systems, the event locator circuit 122 also compares the detection times of the paired events to identify a segment of the straight line, further localizing the event. Coincident event pairs, and their location, are recorded by the event locator circuit 122 as a coincidence data packet that is communicated through a communication link to a sorter 130 in an image reconstruction processor 108.

The image reconstruction processor 108 includes the sorter 130, a memory module 132, an image CPU 134, an array processor 136 and a back-plane bus 138. The sorter 130 identifies intersections of the straight lines or line segments passed from the event locator circuit 122, and organizes the intersections into 3D data grouped by "voxels" (subvolumes within the scanner field of view). The sorter 130 further assigns to each voxel an "intensity" based on the number of intersections within the voxel. In one exemplary embodiment, the sorter 130 organizes the 3D intensity data (or sinogram) as a data array 140. The data array 140 is stored in the memory module 132. The array processor 136 receives the data array 140 as an input and reconstructs images in the form of image arrays 142. The resulting image arrays 142 are stored in memory module 132. The image CPU 134 controls communication of the image arrays 142 from the memory module 132 through the back-plane bus 138 back to the operator workstation 104 via the communication link 110.

The operator workstation 104 includes a CPU 144, a display device 146 and an input device 148. The CPU 144 receives the image arrays 142 from the communication link 110 and receives inputs, e.g., user commands, from an input device 148. The input device 148 may be, for example, a keyboard, mouse, or a touch-screen panel. Through the input device 148 and associated control panel switches, the operator can control the calibration of PET scanner 101, the configuration of PET scanner 101, and the positioning of target 114 for a scan. The input device 148 can also be used to control the processing performed by the image CPU 134 by specifying, for example, the filters and processing methods used in the reconstruction. Similarly, the operator can use the input device 148 to control how the CPI 144 displays the image arrays 142 on the display device 146. For example, the input device 148 can be used to select different algorithms, filters, or maps for attenuation correction of PET images.

Figure 2:
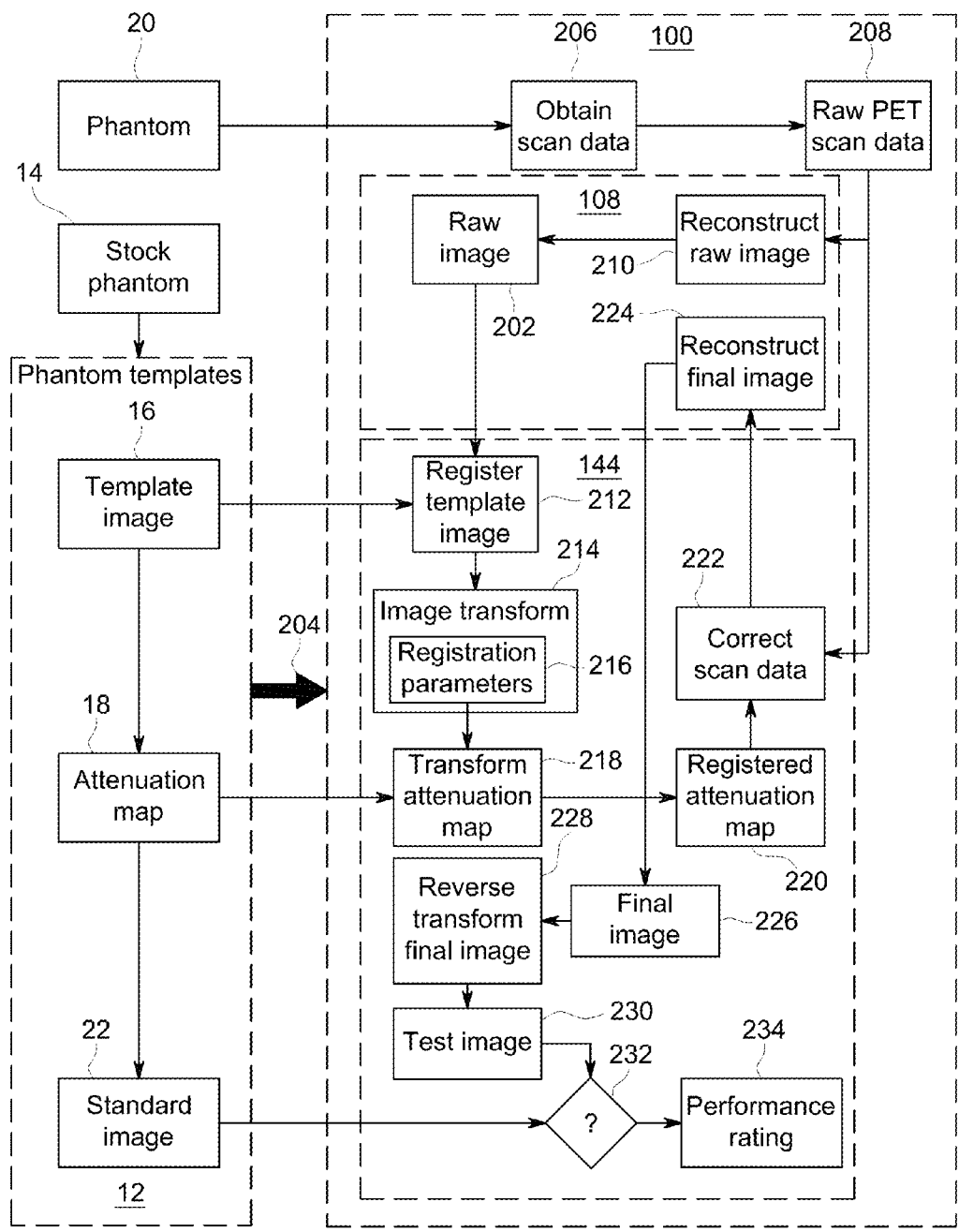
FIG. 2 shows a flow chart of a process for attenuation correction of a PET phantom image, according to one aspect of the present invention.

FIG. 2 shows an exemplary process 200 for attenuation correction of a non-attenuation corrected ("non-AC") PET phantom raw image 202, according to one aspect of the present invention. In the exemplary process 200, the exemplary imaging system 100 is provided 204 with pre-existing phantom templates 12 that correspond to a stock PET phantom 14. The phantom templates 12 include a non-AC PET template image 16 of the stock phantom 14, and a photon (gamma ray) attenuation map 18 of the stock phantom 14.

The attenuation map 18 can be obtained, for example, by undertaking a CT scan of the stock phantom. Alternatively, the attenuation map 18 can be obtained by generating a computer model of the stock phantom that defines the relevant physical and radiologic parameters and locations of constituent materials; then calculating by finite elements, ray-trace, or similar methods the photon attenuation at relevant frequencies through each region of material. The attenuation map 18 can be in various formats, including, by way of example, CT image voxels or a space array of 511 kev attenuation coefficient mu-values.

The imaging system 100 is operated to obtain 206 raw PET scan data 208 (corresponding to the event data packets, discussed above with reference to FIG. 1) from a scanned phantom 20 of "like type" as the stock phantom 14. As used herein, the term "like type" refers to phantoms of the same general configuration. For example, if the pre-existing phantom templates 12 corresponded to a stock phantom 14 such as the NEMA IEC Phantom Set, manufactured by Data Spectrum Corporation, then the scanned phantom 20 would also need to be a NEMA IEC Phantom Set.

Using conventional algorithms (implemented, for example, by the data acquisition processor 106 and the image reconstruction processor 108), the imaging system 100 reconstructs 210 the raw image 202 from the scan data 206. The step of reconstructing 210 can be accomplished, for example, by the image reconstruction processor 108. The imaging system 100 then registers 212 the pre-existing non-AC template image 16 to the non-AC raw image 202. The step of registration 212 can be accomplished, for example, by the CPU 144 at the operator workstation 104.

In the process of registering 212, the imaging system 100 generates an image transform 214 that is described by a set of registration parameters 216. The image transform 214 may be a rigid transform, i.e., one in which dimensional proportionality is conserved. The registration parameters 216 may include, for example, a scaling factor; axial translation factors; and angular rotation factors about one or more axes.

The imaging system 100 then transforms 218 the pre-existing attenuation map 18 according to the registration parameters 216, in order to generate a registered attenuation map 220, which is aligned with the raw image 102. Using the registered attenuation map 220, the imaging system 100 corrects 222 the scan data 106 and reconstructs 224 a finished (attenuation corrected or "AC") image 300 from the corrected scan data. The steps of transforming 218, and correcting 222 also can be accomplished in the CPU 144. In an embodiment, the step of reconstructing 224 may be accomplished by the image reconstruction processor 108.

By reverse transforming 228 the finished image 300, using an inversion of the image transform 214, the imaging system 100 also can generate a test image 230 that can be compared 232 one-to-one against a standard (AC) image 22 of the stock phantom 14. The steps of reverse transforming 228 and comparing 232 also can be accomplished in the CPU 144 to produce a one-or-more-dimensional numerical performance rating 234 of the imaging system 100. For example, the performance rating 234 may be a vector describing differences in voxel size, intensity, and contrast between the test image 230 and the standard image 22.

Figure 3:
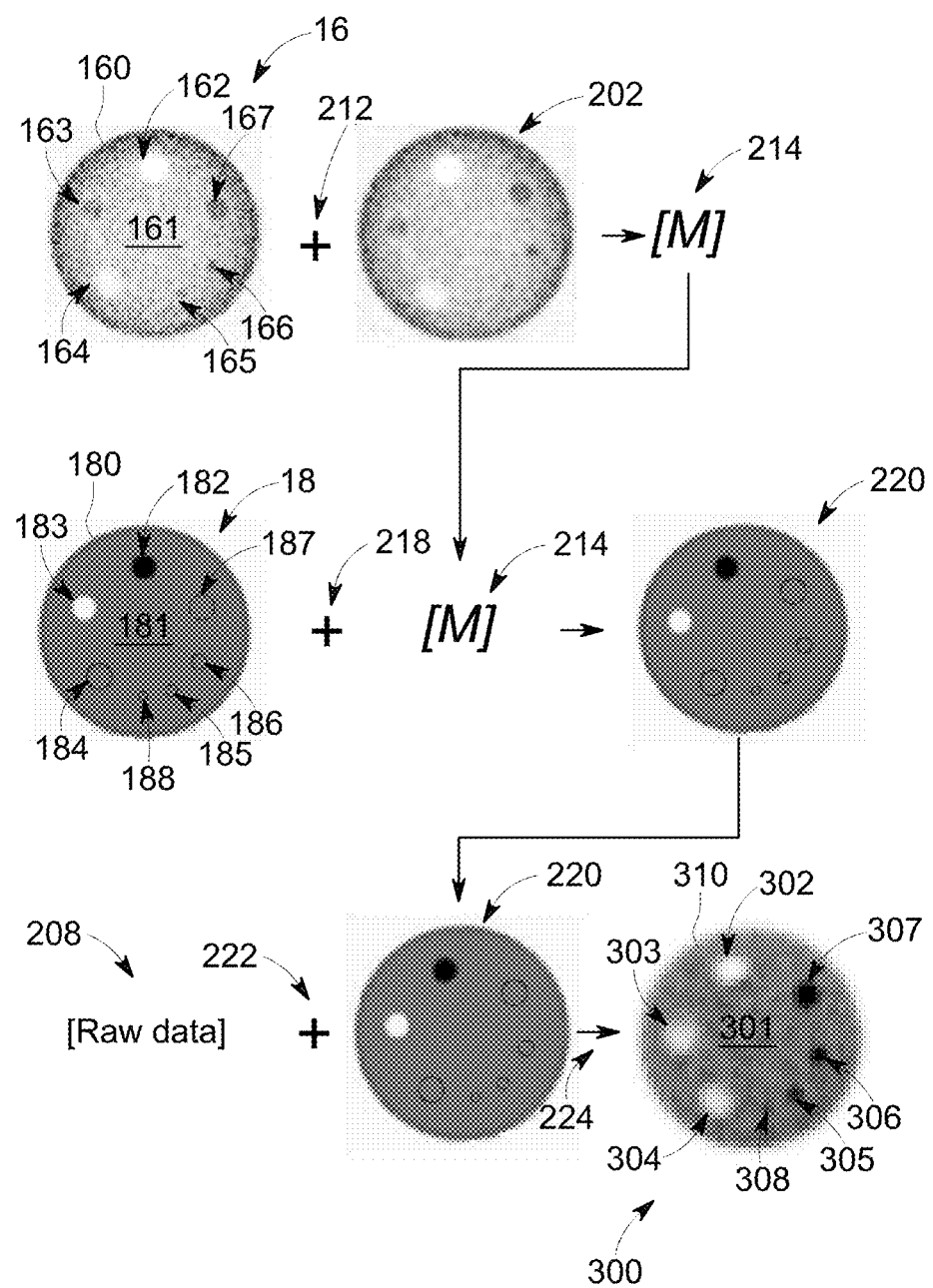
FIG. 3 shows a sequence of images generated during an exemplary implementation of the process shown by FIG. 2.

FIG. 3 illustrates in sequence a set of images produced by an implementation of the process discussed with reference to FIG. 1. First, the template image 16 and the attenuation map 18 are provided.

The template image 16 shows a shell 160 of the stock phantom 14, which is filled with water 161. Proceeding counterclockwise from the top, the template image 16 shows a Teflon (high attenuation, zero emissions) insert 162, an air-filled (low attenuation, zero emissions) insert 163, and a "cool" (natural background radioactivity) water-filled insert 164 (moderate attenuation, zero emissions). Continuing counterclockwise, the template image 16 also shows a sequence of four "hot" (enhanced radioactivity) water-filled inserts 165, 166, 167 (moderate attenuation, high emissions). The "hot" water-filled inserts vary at least in diameter, which is the key parameter affecting emission and attenuation in an axial slice such as the template image 16.

The attenuation map 18 likewise shows a shell 180 of the stock phantom 14. It should be noted that different numbering is used for the PET data or attenuation data relative to identical structures, because the shell 180 appears differently in PET than in CT or other attenuation scanning modes. Accordingly, in the attenuation map 18, water 181 fills the stock phantom shell 180, and a high attenuation insert 182 is shown at top. Proceeding counterclockwise around the attenuation map 18, there are the air-filled (low attenuation) insert 183, the "cool" water-filled (moderate attenuation) insert 184, and the sequence of "hot" water-filled inserts 185, 186, 187. Additionally, a fourth "hot" water insert 188, of smaller diameter, can be clearly seen in the attenuation map 18.

The raw image 202 is registered 212 with the template image 16 to produce the image transform 214 (shown in FIG. 3 as a transform matrix "[M]"). The attenuation map 18 is transformed 218 according to the image transform 214 to produce the registered attenuation map 220. The registered attenuation map 220 is used to correct 222 the scan data 208, which is reconstructed 224 to produce the finished image 300.

The finished image 300 shows, within a shell 310, a volume of water 301; a high attenuation insert 302; an air-filled (low attenuation) insert 303; a "cool" water-filled (moderate attenuation) insert 304; and a sequence of "hot" water-filled inserts 305, 306, 307, 308. These image components correspond to the scanned phantom 20.

In view of the above, embodiments of the invention provide reliable, repeatable, and accurate techniques for attenuation correction of PET images of conventional phantom bodies. Further embodiments of the invention may also provide for attenuation correction of PET images of custom phantom bodies. Embodiments of the invention can enable commercial PET scanners to produce AC PET images of phantom bodies. Such embodiments are particularly useful for accomplishing PET calibration procedures, which may be improved by availability of accurate attenuation corrected phantom images. Additionally, embodiments of the invention enable high-quality reconstructions of attenuation corrected images, thereby enhancing performance of commercial PET scanners relative to specifications for phantom image quality.

In embodiments of the invention, a method for attenuation correction of a phantom image in a PET imaging system includes obtaining raw scan data, a non attenuation corrected template image of a stock phantom of like type to the scanned phantom, and an attenuation map of the stock phantom. The method further includes generating a non-attenuation corrected raw image of a scanned phantom based on the raw scan data, registering the template image and attenuation map to the raw image through a rigid image transform, and applying the registered attenuation map to the raw scan data to enable reconstruction of an attenuation corrected final image. In embodiments, the step of registering the template image and attenuation map to the raw image includes creating a rigid image transform in the PET imaging system by a comparison of the template image to the raw image.

In some embodiments, the attenuation map is obtained from a CT scan of the stock phantom. In other aspects, the attenuation map is obtained from a computer ray-trace model of the stock phantom. In other aspects, the attenuation map is obtained from a computer finite element model of the stock phantom. In other aspects, the attenuation map is obtained from a Dixon sequence MR scan. In some aspects, the attenuation map is in a format of CT image voxels; in other aspects, the attenuation map is in a format of space-arrayed attenuation coefficient mu-values.

In embodiments of the invention, a PET imaging system includes a detector ring configured to produce signals indicating the detection of photons produced by positron-electron recombination and a processor connected in communication with the detector ring. The processor is configured to obtain a non-attenuation corrected template image and an attenuation map of a stock phantom; obtain raw scan data of a scanned phantom of like type to the stock phantom; generate a non-attenuation corrected raw image of the scanned phantom based on the raw scan data; register the template image and attenuation map to the raw image; and generate a attenuation corrected final image from the raw scan data, using the registered attenuation map.

In embodiments, the processor registers the template image and attenuation map to the raw image by developing a rigid image transform to register the template image with the raw image and applying the rigid image transform to register the attenuation map with the raw image. In embodiments, the processor is configured to obtain the attenuation map from stored data of a CT scan of the stock phantom. In other embodiments, the processor is configured to obtain the attenuation map from a computer ray-trace model of the stock phantom. In yet other embodiments, the processor is configured to obtain the attenuation map from a computer finite element model of the stock phantom. In other embodiments, the processor is configured to obtain the attenuation map from stored data of a Dixon sequence MR scan. In certain embodiments the processor is configured to process the attenuation map in a format of CT image voxels; in other embodiments, the processor may be configured to process the attenuation map in a format of space-arrayed attenuation coefficient mu-values.

In embodiments, a processor, for communication with a detector ring that produces signals indicating the detection of photons from positron-electron recombination, is configured to receive as raw scan data the signals produced by the detector ring; generate a non-attenuation corrected raw image of a scanned phantom inserted through the detector ring, based on the raw scan data; obtain a non attenuation corrected template image and a computer model of a stock phantom, which is of like type to the scanned phantom; register the template image of the stock phantom to the raw image of the scanned phantom using a rigid image transform; and generate an attenuation corrected final image from the raw image, using the computer model of the stock phantom. In embodiments, the processor is further configured to create the rigid image transform by comparison of the template image to the raw image.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their targets. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice embodiments of the invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of the elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described methods and systems, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method for attenuation correction of a phantom image in a PET/MR imaging system comprising:
    performing a PET scan on a phantom;
    obtaining raw scan data from the scanned phantom via the PET scan;
    generating from the raw scan data a non-attenuation corrected raw image of the scanned phantom;
    obtaining a non attenuation corrected template image of a stock phantom and an attenuation map of the stock phantom, the stock phantom of like type to the scanned phantom;
    registering the template image and attenuation map to the raw image through a rigid image transform; and
    applying the registered attenuation map to the raw scan data to enable reconstruction of an attenuation corrected final image.

2. The method of claim 1, further comprising
    creating the rigid image transform in the PET imaging system by comparison of the template image to the raw image.

3. The method of claim 1, wherein the attenuation map is obtained from a CT scan of the stock phantom.

4. The method of claim 1, wherein the attenuation map is obtained from design data of the stock phantom.

5. The method of claim 4, wherein the attenuation map is obtained from a computer finite element model of the stock phantom.

6. The method of claim 4, wherein the attenuation map is obtained from a computer ray-trace model of the stock phantom.

7. The method of claim 1, wherein the attenuation map is in a format of CT image voxels.

8. The method of claim 1, wherein the attenuation map is in a format of space-arrayed attenuation coefficient mu-values.

9. A PET/MR imaging system comprising:
    a detector ring configured to produce signals indicating the detection of photons produced by positron-electron recombination;
    a processor connected in communication with the detector ring; and
    wherein the processor is configured to obtain a non attenuation corrected template image of a stock phantom; to obtain an attenuation map of the stock phantom; to perform a PET scan of a phantom to generate a raw non-attenuation corrected image of the scanned phantom of like type to the stock phantom; to register the template image and attenuation map to the raw image; and to generate an attenuation corrected final image from the raw scan data, using the registered attenuation map, and without relying on MR data.

10. The system of claim 9 wherein the processor registers the attenuation map to the raw image by first developing a rigid image transform to register the template image with the raw image and then applying the rigid image transform to the attenuation map.

11. The system of claim 9, wherein the processor is configured to obtain the attenuation map from stored data of a CT scan of the stock phantom.

12. The system of claim 9, wherein the processor is configured to obtain the attenuation map from design data of the stock phantom.

13. The system of claim 12, wherein the processor is configured to obtain the attenuation map from a computer finite element model of the stock phantom.

14. The system of claim 12, wherein the processor is configured to obtain the attenuation map from a computer raytrace model of the stock phantom.

15. The system of claim 9, wherein the processor is configured to process the attenuation map in a format of CT image voxels.

16. The system of claim 9, wherein the processor is configured to process the attenuation map in a format of space-arrayed attenuation coefficient mu-values.

17. A processor for communication with a detector ring that produces signals indicating the detection of photons from positron-electron recombination, wherein the processor is configured to:
  initiate a PET scan of a phantom inserted through the detector ring;
  receive as raw scan data the signals produced by the detector ring during the PET scan;
  generate a non-attenuation corrected raw image of the scanned phantom based on the raw scan data;
  obtain a non attenuation corrected template image of a stock phantom and to obtain a computer model of the stock phantom, which is of like type to the scanned phantom;
  register the computer model of the stock phantom to the raw image using a rigid image transform; and
  generate an attenuation corrected final image from the raw image, using the computer model of the stock phantom, and without relying on MR data.

18. The processor of claim 17 further configured to create the rigid image transform by comparison of the template image to the raw image.

* * * * *